(12) United States Patent
Tillman et al.

(10) Patent No.: US 10,413,301 B2
(45) Date of Patent: Sep. 17, 2019

(54) PERFUSION DEVICE FOR TREATING AN INJURED BLOOD VESSEL

(71) Applicant: University of Pittsburgh—Of the Commonwealth System of Higher Education, Pittsburgh, PA (US)

(72) Inventors: Bryan W. Tillman, Pittsburgh, PA (US); William W. Clark, Wexford, PA (US); Sung Kwon Cho, Pittsburgh, PA (US); Youngjae Chun, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 433 days.

(21) Appl. No.: 14/904,063

(22) PCT Filed: Jul. 10, 2014

(86) PCT No.: PCT/US2014/046224
§ 371 (c)(1),
(2) Date: Jan. 8, 2016

(87) PCT Pub. No.: WO2015/006607
PCT Pub. Date: Jan. 15, 2015

(65) Prior Publication Data
US 2016/0157868 A1      Jun. 9, 2016

Related U.S. Application Data

(60) Provisional application No. 61/845,896, filed on Jul. 12, 2013.

(51) Int. Cl.
*A61B 17/12* (2006.01)
*A61F 2/966* (2013.01)
(Continued)

(52) U.S. Cl.
CPC ...... *A61B 17/12109* (2013.01); *A61B 5/0215* (2013.01); *A61B 5/02141* (2013.01);
(Continued)

(58) Field of Classification Search
CPC .............. A61B 17/12109; A61B 90/98; A61B 5/02141; A61B 5/0215; A61B 17/12031;
(Continued)

(56) References Cited

U.S. PATENT DOCUMENTS 5,226,913 A * 7/1993 Pinchuk .................... A61F 2/88
140/71 R
5,599,306 A 2/1997 Klein et al.
(Continued)

OTHER PUBLICATIONS

Byun et al., "Wireless EWOD (Electrowetting-on-Dielectric) Device Using Planar Coils," 16th International Conference on Miniaturized Systems for Chemistry and Life Sciences, Okinawa, Japan, pp. 344-346, Oct. 28-Nov. 1, 2012.
(Continued)

*Primary Examiner* — Manuel A Mendez
(74) *Attorney, Agent, or Firm* — Klarquist Sparkman, LLP

(57) ABSTRACT

The present disclosure concerns embodiments of an implantable perfusion device that can be implanted in an injured blood vessel to control bleeding without occluding the vessel. In one specific implementation, the perfusion device can be implanted percutaneously into a patient's descending aorta to control bleeding at the site of a ruptured portion of the aorta (known as torso hemorrhage) while still allowing for the antegrade flow of blood from a location upstream of the ruptured portion of the aorta to a location downstream of the ruptured portion of the aorta. The perfusion device can be left inside the patient as the patient is transported to a medical facility where the injury can be repaired. Following
(Continued)

repair of the vessel, the perfusion device can be withdrawn from the patient.

28 Claims, 11 Drawing Sheets

(51) Int. Cl.
*A61B 5/021* (2006.01)
*A61B 5/0215* (2006.01)
*A61B 90/98* (2016.01)
*G06K 7/10* (2006.01)
*A61F 2/07* (2013.01)
*A61F 2/95* (2013.01)
*A61B 17/00* (2006.01)
*A61B 90/00* (2016.01)

(52) U.S. Cl.
CPC .... *A61B 17/1204* (2013.01); *A61B 17/12031* (2013.01); *A61B 17/12036* (2013.01); *A61B 17/12136* (2013.01); *A61B 90/98* (2016.02); *A61F 2/966* (2013.01); *G06K 7/10366* (2013.01); *A61B 2017/00115* (2013.01); *A61B 2090/397* (2016.02); *A61B 2090/3966* (2016.02); *A61F 2/07* (2013.01); *A61F 2002/9511* (2013.01)

(58) Field of Classification Search
CPC .......... A61B 17/12036; A61B 17/1204; A61B 17/12136; A61F 2/966; G06K 7/10366; A61M 25/10; A61M 25/104
See application file for complete search history.

(56) References Cited

U.S. PATENT DOCUMENTS

| 6,190,355 | B1 | 2/2001 | Hastings | |
|---|---|---|---|---|
| 6,280,414 | B1 | 8/2001 | Shah et al. | |
| 6,547,760 | B1 | 4/2003 | Samson et al. | |
| 6,840,956 | B1* | 1/2005 | Wolinsky | A61B 5/02014 600/454 |
| 7,429,920 | B2* | 9/2008 | Smythe | A61B 5/0031 340/539.12 |
| 8,167,930 | B2* | 5/2012 | Allen | A61F 2/06 623/1.24 |
| 2006/0004442 | A1* | 1/2006 | Spenser | A61F 2/2409 623/2.11 |
| 2009/0281419 | A1 | 11/2009 | Troesken et al. | |
| 2010/0270640 | A1* | 10/2010 | Dekker | H01L 23/49833 257/528 |
| 2011/0264039 | A1 | 10/2011 | Thielen et al. | |

OTHER PUBLICATIONS

Hsiai et al., "Micro Sensors: Linking Real-Time Oscillatory Shear Stress with Vascular Inflammatory Responses," *Annals of Biomedical Engineering*, vol. 32, No. 2, pp. 189-201, Feb. 2004.
Yan and Pan, "An Ultra-High Sensitivity, Capacitive Pressure Sensor Using Ionic Liquid," MEMS 2011, Cancun Mexico, pp. 557-560, Jan. 23-27, 2011.
Yoon et al., "Inherent Amplitude Demodulation of an AC-EWOD (Electrowetting on Dielectric)," The Royal Society of Chemistry, *Lab Chip*, 13, pp. 662-668, 2013.
International Search Report of the International Searching Authority, dated Oct. 31, 2014, for corresponding International Application No. PCT/GB2014/046224, 4 pages.
Written Opinion of the International Searching Authority, dated Nov. 3, 2014, for corresponding International Application No. PCT/GB2014/046224, 10 pages.

* cited by examiner

Example frequency response plot of RLC circuit.

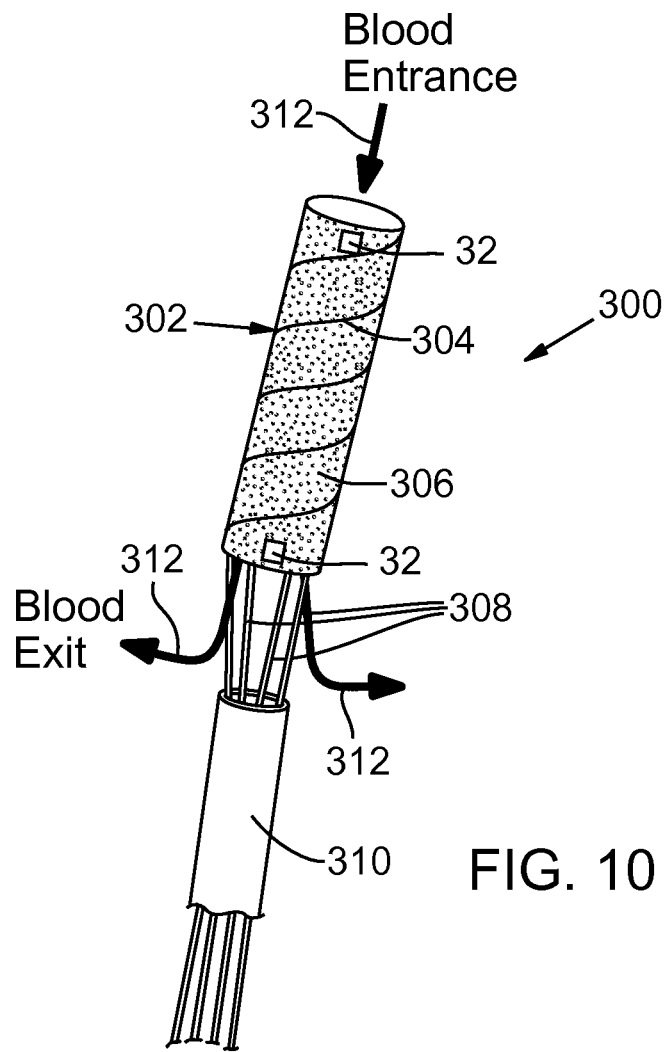
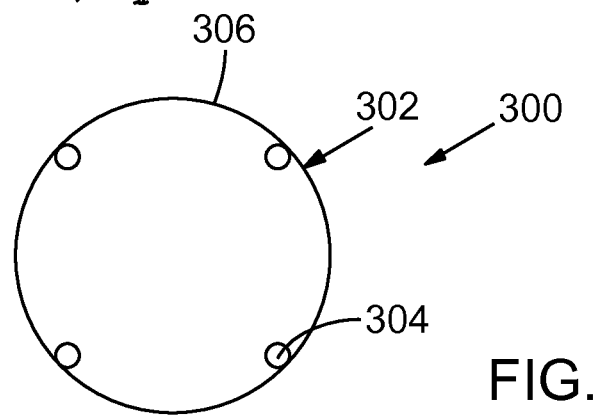

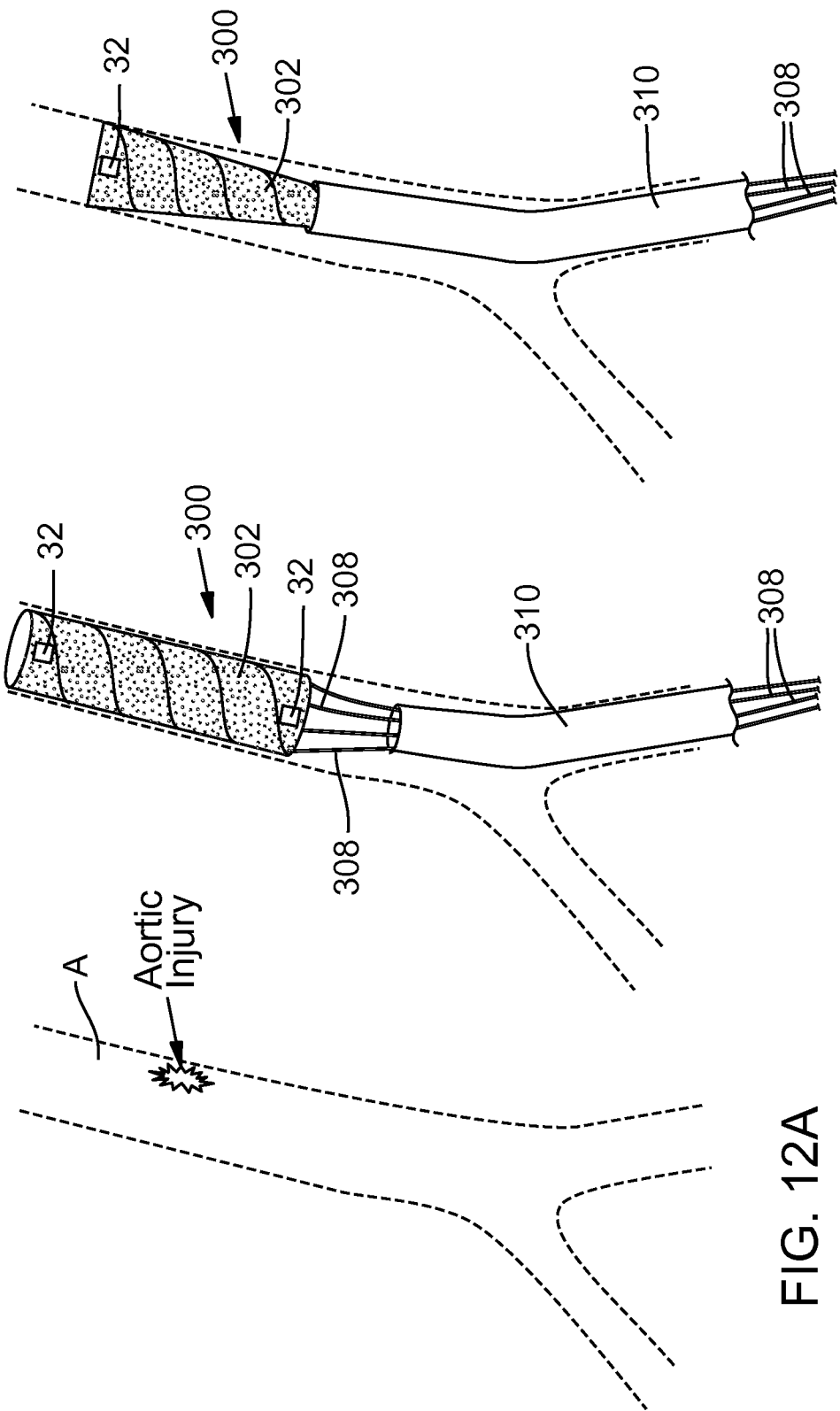

Examples of signal output are shown with increasing lateral distance (0 to 4 cm) of the tag from the reader antenna. Signal intensity is greatest when the center of the reader directly overlies the RFID tag (0 cm).

PERFUSION DEVICE FOR TREATING AN INJURED BLOOD VESSEL

CROSS REFERENCE TO RELATED APPLICATIONS

This is the U.S. National Stage of International Application No. PCT/US2014/046224, filed Jul. 10, 2014, which in turn claims the benefit of U.S. Provisional Application No. 61/845,896, filed Jul. 12, 2013, both of which are incorporated herein by reference.

FIELD

The present disclosure concerns embodiments of an implantable perfusion device that can be implanted in an injured blood vessel to minimize or prevent bleeding without occluding the vessel.

BACKGROUND

Hemorrhage from penetrating injuries to the torso represents between 19-28% percent of military injuries with increases noted among the most recent conflicts. Among modern military injuries regarded as potentially survivable, over 80% are related to hemorrhage. More specifically, noncompressible hemorrhage related to injury of the torso represents half of all potentially survivable injuries. The most serious hemorrhagic injuries of the torso would be expected from injuries to the aorta.

In the current era of aortic stent grafts, repair of these injuries can be relatively straightforward, but only in facilities with proper fixed fluoroscopic imaging equipment and endovascular expertise. Because blood loss can be rapid from these injuries, the major issue becomes how to transport patients from the location where the injury is sustained (e.g., the front line of a battlefield) to a medical facility before they have sustained significant blood loss. Aside from the obvious hemodynamic effects of hemorrhage, blood loss is strongly associated with ensuing coagulopathy, multi-organ failure as well as initiating conditions such as Systemic Inflammatory Response Syndrome. These increase the acute complexity of trauma patients, extend long term intensive care management, and increase the risks for other complications such as long term organ failure, even despite eventual replacement of lost blood volume.

Accordingly, a significant need exists for devices and methods that can be used to minimize or prevent blood loss from injuries to the aorta until the patient can be transported to a medical facility where the injury can be repaired.

Open repair of perivisceral aortic pathology is complicated by issues of distal ischemia during repair in both military (traumatic) and civilian (aneurysm) settings. The conventional clamp and sew approach increases the risk for organ failure, lower extremity ischemia and paraplegia. Alternately, distal aortic perfusion by means of a left heart bypass entails increased complexity including additional perfusion equipment, increased expertise on the part of the surgeon and additional operative exposure. Further, the necessary equipment may not be available at many facilities. Accordingly, a significant need exists for improved, easy to use devices that can allow for perfusion of arteries downstream of an injured or diseased portion of the aorta during complex open aortic repair.

SUMMARY

The present disclosure concerns embodiments of an implantable perfusion device that can be implanted in an injured blood vessel to control bleeding without occluding the vessel. In one specific implementation, the perfusion device can be implanted percutaneously into a patient's descending aorta to control bleeding at the site of a ruptured portion of the aorta (known as torso hemorrhage) while still allowing for the antegrade flow of blood from a location upstream of the ruptured portion of the aorta to a location downstream of the ruptured portion of the aorta. The perfusion device can be left inside the patient as the patient is transported to a medical facility where the injury can be repaired. Following repair of the vessel, the perfusion device can be withdrawn from the patient.

In particular embodiments, the perfusion device generally comprises at least one elongated member, such as an elongated shaft, extending from a proximal end portion to a distal end portion. A handle can be coupled to the proximal end portion of the at least one elongated member. An expandable sealing member can be affixed to the distal end portion of the elongated member. The sealing member has a blood-impermeable surface configured to form a seal along an inner surface of the blood vessel adjacent a ruptured portion of the blood vessel when the sealing member is deployed from a radially collapsed state to a radially expanded, deployed state inside the vessel to control bleeding through the ruptured portion of the vessel. The sealing member permits the antegrade flow of blood through the sealing member from a location upstream of the ruptured portion of the vessel to a location downstream of the ruptured portion of the vessel. The sealing member desirably is further configured to be radially collapsible from the deployed state to the radially collapsed state for removal of the sealing member from the patient's body.

In one implementation, the expandable sealing member comprises an inflatable balloon mounted on a shaft. When inflated, the outer surface of the balloon forms a seal against the inner surface of the blood vessel to prevent or minimize bleeding. The shaft has a distal opening, one or more side ports located along the shaft between a proximal end of the balloon and the proximal end portion of the shaft, and a lumen in fluid communication with the distal opening and the one or more side ports such that a perfusion pathway for the flow of blood extends from the distal opening, through the lumen and outwardly through the side ports within the confines of the vessel downstream of the injury.

In another implementation, the sealing member comprises a self-expandable stent or frame and a blood-impermeable sleeve supported by the stent. The stent has a distal opening, a proximal opening, and a lumen in fluid communication with the distal opening and the proximal opening such that a perfusion pathway for the flow of blood extends from the distal opening, through the lumen and outwardly through the proximal opening within the confines of the vessel downstream of the injury.

The perfusion device is particular suited for implantation in the field (e.g., the combat theater or the scene of an accident). As such, the perfusion device desirably has position markers or sensors that allow for proper placement within the injured vessel without the use of conventional fluoroscopy. For example, the perfusion device can have emitters mounted at known locations on the device and which can be detected with a portable, hand-held detector outside the body.

In one representative embodiment, a method of treating a ruptured blood vessel of a patient comprises inserting a perfusion device into the vasculature of the patient. The perfusion device comprises at least one elongated member having a distal end portion and a radially expandable sealing member coupled to the distal end portion of the elongated member. The method further comprises advancing the perfusion device through the patient's vasculature until the sealing member is adjacent the ruptured portion of the blood vessel. The sealing member is then radially expanded such that a blood-impermeable outer surface of the sealing member forms a seal along an inner wall of the blood vessel and covers the ruptured portion of the vessel. The perfusion device provides a perfusion pathway extending from an inlet at a location upstream of the ruptured portion of the vessel through the sealing member to an outlet at a second location downstream of the ruptured portion of the vessel causing antegrade blood to flow into the inlet, through the sealing member, and outwardly through the outlet within the confines of the vessel downstream of the ruptured portion of the vessel.

In another representative embodiment, a method of treating a ruptured blood vessel of a patient comprises inserting a perfusion device into the vasculature of the patient. The perfusion device comprises an elongated shaft having a distal end portion and an inflatable balloon mounted on the shaft distal end portion. The shaft has a distal opening, one or more ports in a side wall of the shaft, and a lumen in fluid communication with the distal opening and the one or more ports. The method further comprising advancing the perfusion device through the patient's vasculature until the balloon is adjacent the ruptured portion of the blood vessel. The balloon is inflated such that an outer surface of the balloon contacts an inner wall of the blood vessel and covers the ruptured portion of the vessel, causing blood to flow into the distal opening, through the lumen, and outwardly through the one or more ports within the confines of the vessel downstream of the injury.

In another representative embodiment, a perfusion device for treating a ruptured blood vessel of a patient comprises an elongated shaft extending from a proximal end portion to a distal end portion, and an inflatable balloon mounted on the distal end portion of the shaft. The balloon has a distal end and a proximal end. The shaft has a distal opening, one or more side ports located along the shaft between the proximal end of the balloon and the proximal end portion of the shaft, and a lumen in fluid communication with the distal opening and the one or more side ports such that a perfusion pathway for the flow of blood extends from the distal opening, through the lumen and outwardly through the side ports. The perfusion device can further comprise one or more RFID tags configured to emit radiofrequency waves through the patient's body to assist in positioning the balloon at a desired location within the patient's vasculature.

In another representative embodiment, a perfusion device for treating a ruptured blood vessel of a patient comprises an elongated shaft extending from a proximal end portion to a distal end portion. The shaft has a distal opening and a lumen in fluid communication with the distal opening. An inflatable balloon, having a distal end and a proximal end, is mounted on the distal end portion of the shaft. The shaft and the balloon are configured to be positioned in the aorta of the patient, and the balloon, when inflated, can form a seal against the inner wall of the aorta upstream of an injured or diseased portion of the aorta to be repaired. The perfusion device further comprises a plurality of blood conduits, each having a distal end portion, a proximal end portion and a lumen extending therebetween. The distal end portion of each conduit is connected to the shaft at a location between the proximal end of the balloon and the proximal end portion of the shaft and is in fluid communication with the lumen of the shaft. The proximal end portion of each blood conduit is configured to be positioned within a respective branch artery of the aorta. In this manner, a pathway for the flow of blood extends from the distal opening of the shaft, through the lumen of the shaft, and through each blood conduit into the branch arteries. The perfusion device can further comprise a plurality of additional balloons mounted on the proximal end portions of respective blood conduits to assist in retaining the proximal end portions in the branch arteries.

The foregoing and other features and advantages of the invention will become more apparent from the following detailed description, which proceeds with reference to the accompanying figures.

BRIEF DESCRIPTION OF THE DRAWINGS

FIG. 10 is a perspective view of a perfusion device, according to another embodiment.

FIG. 11 is a cross-sectional view of the perfusion device of FIG. 10.

FIGS. 12A-12C illustrate the deployment of the perfusion device of FIG. 10 in the descending aorta.

DETAILED DESCRIPTION

Figure 1:
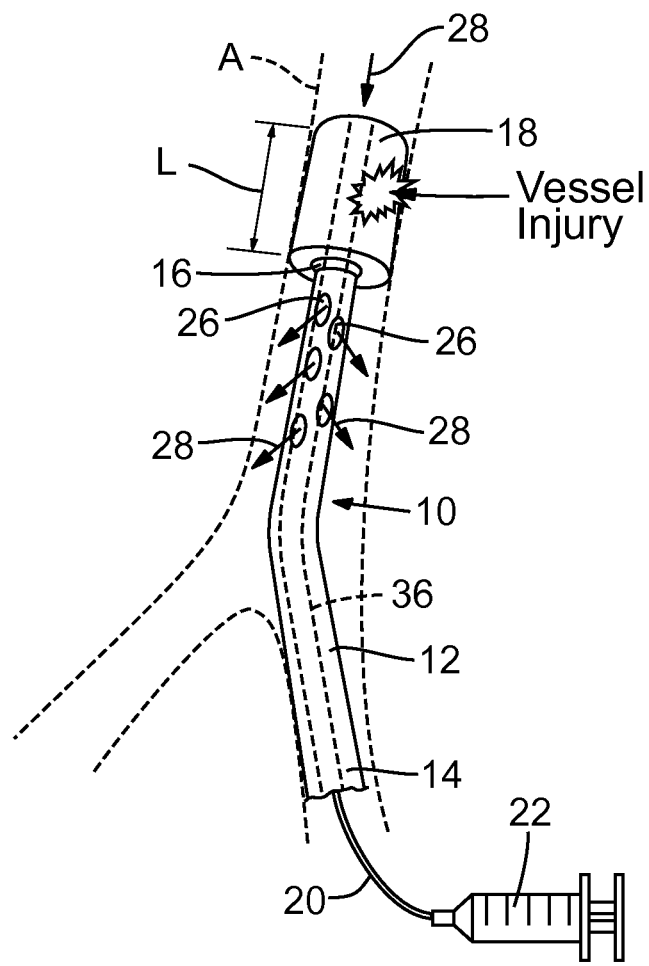
FIG. 1 is a perspective view of a perfusion device, according one embodiment, shown deployed within the descending aorta of a patient.
Figure 2:
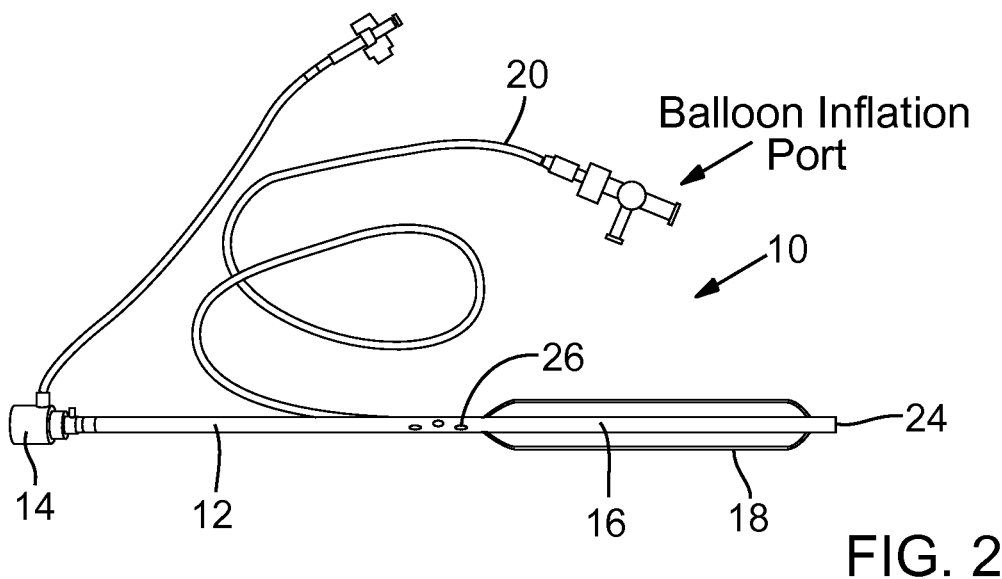
FIG. 2 is a plan view of a perfusion device, according to another embodiment.

FIG. 1 shows a schematic representation of an implantable perfusion device 10, according to one embodiment, implanted in the descending aorta A. FIG. 2 shows a working embodiment of the perfusion device 10. As shown in FIG. 1, the perfusion device 10 can be implanted adjacent an injury to the aorta (e.g., a ruptured portion of the aorta) to prevent or minimize bleeding from the vessel while still allowing blood to perfuse through the device. Although the perfusion device 10 is described in connection with treating an injury to the aorta, it should be understood that the perfusion device 10 also can be implanted in other blood vessels, as well other tubular organs of the body.

The perfusion device 10 in the illustrated embodiment comprises an elongated shaft 12 having a proximal end portion 14 and a distal end portion 16. An expandable sealing member in the form of an inflatable balloon 18 is mounted on the distal end portion 16 of the shaft 12. An inflation conduit 20 has a distal end fluidly connected to the balloon 18 and a proximal end fluidly connected to a source of an inflation fluid, such as the illustrated syringe 22. In use, the syringe 22 transfers a pressurized inflation fluid (e.g., saline) to the balloon to inflate the balloon, as described in greater detail below. The balloon 18 is configured such that when it is inflated, the outer surface of the balloon can contact the inner wall of the aorta A and create a seal around an injury to the vessel to stop or minimize bleeding.

Instead of providing a separate inflation conduit 20, the shaft 12 can be formed with a separate inflation lumen that extends from the balloon 18 to a proximal end of the shaft outside the body. The proximal end of the inflation lumen can be fluidly connected to a source of an inflation fluid (e.g., a syringe 22) to pump the inflation fluid through the inflation lumen and into the balloon 18.

The shaft 12 has a plurality of perfusion ports or apertures 26 proximal to the balloon 18. The shaft 12 has a lumen, or internal passageway, 36 that extends lengthwise of the shaft from a distal opening at a distal end 24 to a location proximal to the ports 26. The perfusion ports 26 are in fluid communication with the lumen of the shaft. Thus, upon deployment within the aorta, a flow path for blood is established through the shaft, in the direction indicated by arrows 28. As shown in FIG. 2, the lumen 36 can terminate at a location intermediate the proximal most port 26 and the proximal end portion 14 of the shaft 12. Alternatively, the lumen 36 can extend the entire length of the shaft 12 and the device includes a valve housed within or coupled to the proximal portion 14 that can be used to seal off the end of the lumen 36 to prevent blood from flowing outside the body.

Typically, although not necessarily, the perfusion device 10 is used to treat temporarily an injury to a blood vessel, such as a vessel rupture, until the patient can be transported to a medical facility where the blood vessel can be repaired. Thus, the perfusion device can be implanted in a patient by, for example, emergency medical personnel in a battlefield or at the scene of an accident. In use, the perfusion device 10 is inserted into the patient's vasculature and advanced until the balloon 18 is in the vicinity of an injury to a blood vessel. FIG. 1, for example, illustrates an injury to the descending aorta A.

The perfusion device 10 can be inserted into a femoral artery and advanced through the patient's vasculature in a retrograde direction until the distal end of the balloon 18 is distal to the location of the injury. The proximal end portion 14 can serve as a handle for manipulating the device and can remain outside the body when the balloon is positioned at the desired deployment location. The balloon 18 can then be inflated, such as by activation of the syringe 22, causing the outer surface of the balloon to contact and apply pressure to the inner wall of the aorta on both sides of the injury (i.e., upstream and downstream of the injury). The balloon 18 creates a seal with the inner wall of the aorta, causing blood to flow through into the distal end 24 of the shaft, through the lumen of the shaft, and outwardly through the perfusion ports 26 (in the direction of arrows 28) within the confines of the vessel downstream of the injury, thereby bypassing the injury. The perfusion device 10 therefore protects against further bleeding while allowing for antegrade flow of blood to organs, extremities and collaterals to the spinal cord. In this manner, the perfusion device can stabilize the patient during transport to a medical facility while minimizing the risk for organ failure, limb ischemia and paralysis. The perfusion device can be removed from the body during surgery to repair the blood vessel by first deflating the balloon and withdrawing the device from the body.

In particular embodiments, the balloon 18 can be long enough to cover substantially the entire descending thoracic aorta of the average human. For example, in certain embodiments, the balloon 18 can have a length L (FIG. 1) of at least 10 cm, and more desirably at least 15 cm. The balloon 18, when inflated, can have an outer diameter in the range of about 1.5 cm to about 2.5 cm, with about 2 cm being a specific example. The lumen of the shaft 12 can have diameter of about 4.0 mm or greater, with 4.3 mm being a specific example.

In some implementations, the perfusion device 10 can be inserted in the body using a conventional guidewire. For example, a guidewire can be inserted first into the patient's vasculature and advanced until the distal end of the guidewire is distal to the location of injury. The perfusion device 10 can then be inserted over the guidewire. The guidewire can extend through the main lumen of the shaft 12. Alternatively, the shaft 12 can have a separate guidewire lumen that extends from the distal end to the proximal end of the shaft.

Figure 3:
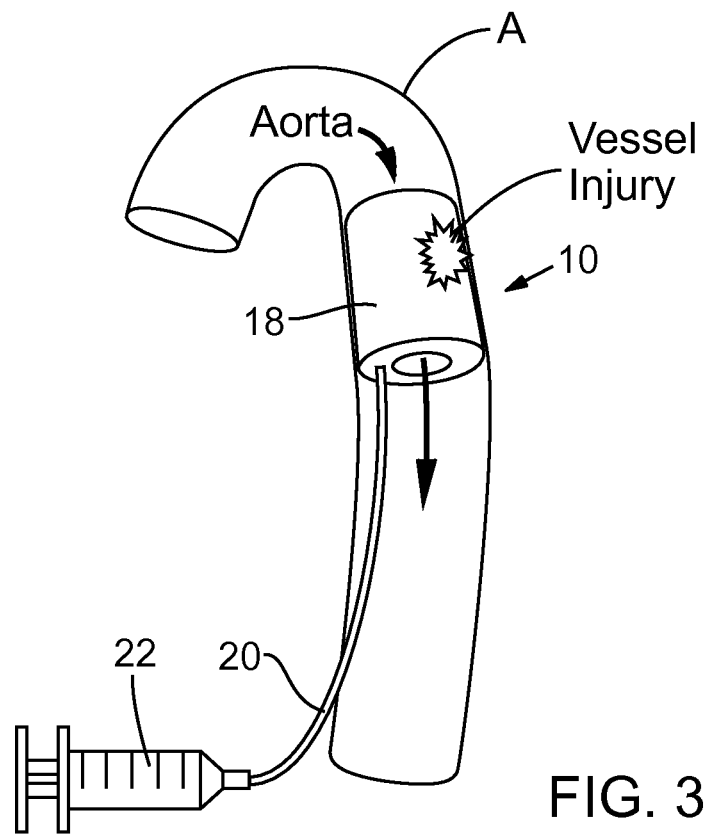
FIG. 3 is a perspective view of a perfusion device, according to another embodiment.

FIG. 3 shows an embodiment of the perfusion device 10 without a shaft 12 shown deployed within the aorta A. In this embodiment, the perfusion device can be introduced and delivered on a separate delivery catheter (not shown), and then subsequently retrieved and removed, such as during surgery to repair the aorta. For example, the balloon can be mounted in a deflated state on the distal end portion of a delivery catheter and then introduced into the patient's vasculature. The balloon 18 can be released from the delivery catheter upon its inflation, after which the delivery catheter can be withdrawn from the body. The balloon 18 in the embodiment of FIG. 3 has an overall tubular shape defining an internal lumen or passageway through which blood can flow when inflated.

Figure 4:
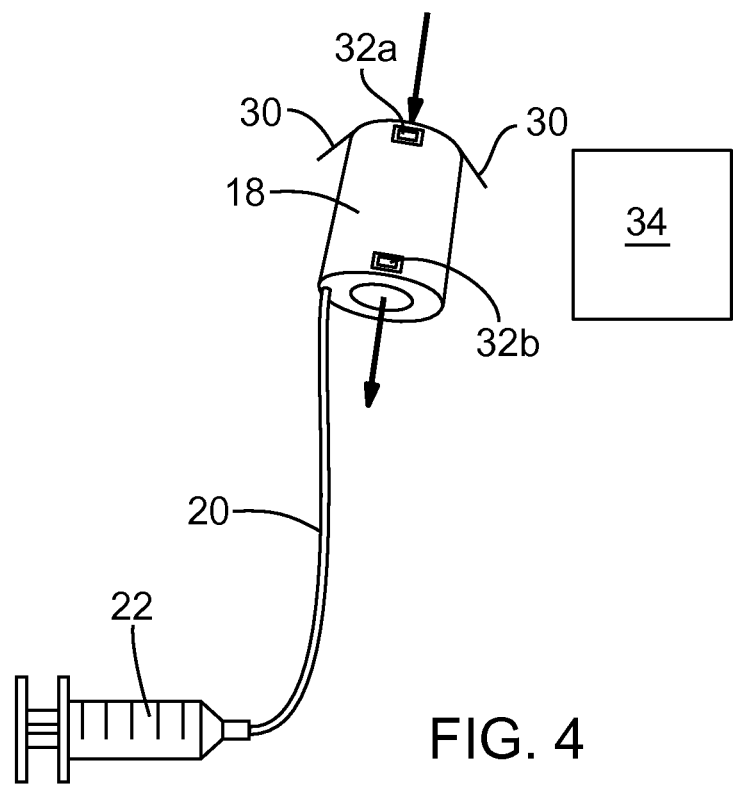
FIG. 4 is a perspective view of a perfusion device, according to another embodiment.

FIG. 4 shows another embodiment of the perfusion device 10 having one or more anchors 30 mounted on the balloon 18. The anchors 30 are positioned to engage the vessel wall to assist in anchoring the balloon in place within the vessel against blood pressure. The anchors 30 can comprise barbs that are configured to penetrate the surrounding tissue when the balloon is inflated. The anchors 30 can be made of any of various suitable biocompatible metals or polymeric materials. In one specific implementation, the anchors 30 can be made of a shape-memory, self-expanding material, such as Nitinol, and can be configured to expand radially from a stowed position for delivery to a deployed position extending away from the balloon for engaging the vessel wall.

As shown in FIG. 4, the perfusion device 10 can also include one or more position markers 32a, 32b that are detectable outside of the body to assist in positioning the balloon 18 relative to the vessel injury. In the illustrated embodiment, the device is shown as having a single distal marker 32a mounted at the distal end of the balloon and a single proximal marker 32b mounted at the proximal end of the balloon. However, a greater or fewer number of markers can be used. For example, a plurality of markers can be spaced circumferentially around each of the distal and proximal ends of the balloon. It should be understood that the anchors 30 and/or the markers 32 also can be implemented in the embodiment shown in FIGS. 1 and 2. Also, the position markers 32 can be mounted at other convenient locations on the perfusion device. For example, a perfusion device can include one or more position markers 32 mounted on the shaft 12 (e.g., a distal position marker mounted on the shaft 12 distal to the balloon 18 and a proximal position marker mounted on the shaft 12 proximal to the balloon 18).

In some embodiments, the position markers 32 can comprise magnets or magnetic material. In applications where fluoroscopy is available, the position markers 32a, 32b can be any of various radiopaque materials known in the art, including any suitable biocompatible metals or alloys (e.g., stainless steel). In such cases, the balloon 18 can be positioned relative to the injury under the guidance of a fluoroscope. Of course, fluoroscopy typically is not available where injuries occurs (e.g., in a battlefield).

Hence, in particular embodiments, the position markers 32a, 32b can comprise passive or active emitters that can emit electromagnetic waves through the body and a corresponding external detector or monitor 34 (FIG. 4) can be used to receive the electromagnetic waves from the emitters and provide visual and/or audible feedback to a user indicating the position of the markers inside the body. In particular embodiments, for example, the position markers can be emitters that can emit radiofrequency waves, such as radiofrequency identification (RFID) tags. The position markers can be, for example, RFID microsensors or microsensors that are also configured to measure one or more hemodynamic or other physiological parameters of the patient, such as blood pressure and heart rate. In alternative embodiments, the device 10 includes one or more position sensors and one or more additional separate sensors that are configured to measure one or more physiological parameters of the patient. The detector 34 desirably is a hand held unit and is powered by batteries or another lightweight, portable power supply to facilitate use in the field.

Figure 5:
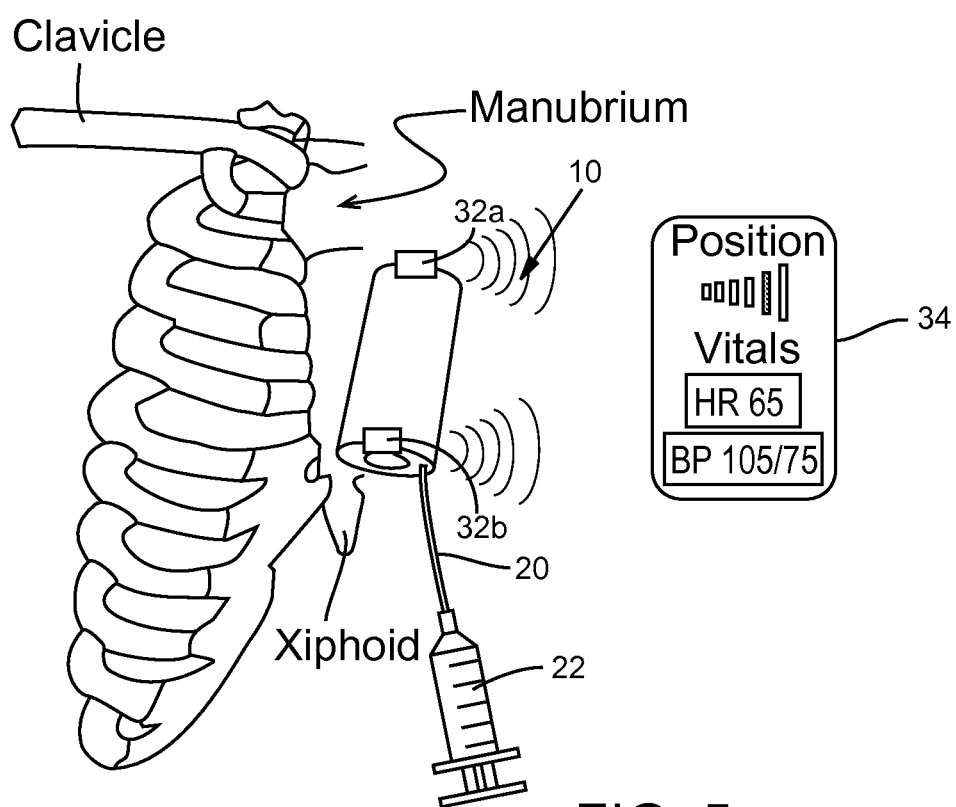
FIG. 5 is perspective view of the perfusion device of FIG. 4, shown being used with an external detector or monitor.

In the field (e.g., the combat theater), it is expected that placement typically will be performed under adverse conditions and by persons without advanced vascular experience. Accordingly, the emitters can allow for a rapid positioning between externally visible anatomic landmarks. As depicted in FIG. 5, for example, shows the placement of the device 10 at a location within the descending aorta between the xiphoid process and the manubrium. The xiphoid process can be used as a landmark for the celiac artery and the manubrium can be used as a landmark for the subclavian artery. Using these external bony landmarks, the user can position the distal end of the balloon 18 downstream of the subclavian artery and the proximal end of the balloon 18 upstream of the celiac artery to avoid obstructing these arteries.

The operating frequencies of the RFID tags and the detector 34 can be selected for detecting radiofrequency waves within several centimeters from the source of the waves. For example, frequencies in a low range (LF, 125-135 kHz) or a high range (HF, 13.56 MHz) can be used for communication within several centimeter separations. Detection of the RFID tags within the body can be accomplished in either a passive communication mode (the detector 34 sends a carrier signal that is received and modulated by an RFID tag 32, which acts as a transponder and sends an identifying signal back to the detector) or in an active mode (both the monitor 34 and RFID tags 32 generate their own fields). In either case, the signal strength read by the detector 34 is a function of the distance between the detector and a tag. When the detector 34 is directly over a tag 32, the signal strength is maximized, thereby enabling the user to determine the location of the tag with respect to external body landmarks.

A high frequency (HF) tag is advantageous in that it requires only a few wire turns as compared to a low frequency (LF) tag, which typically requires a hundred or more turns, resulting in a large axial dimension. Thus, the antenna pattern for a HF tag can be formed (printed) on a planar substrate, or directly on the balloon 18, using MEMS technology. In particular embodiments, an RFID tag 32 can comprise the control circuit of a commercially available RFID tag chip (e.g., a model NTAG203 from NXP Semiconductors) electrically connected to an antenna formed on the balloon 18 or on a separate layer mounted on the balloon.

As noted above, the perfusion device 10 can include one or more physiological sensors, such as a wireless blood pressure sensor. The blood pressure sensor desirably can detect blood pressure in a range of 0-150 mm Hg (0-20 kPa). In certain embodiments, the blood pressure sensor can comprise a pressure sensing device that measures the deflection of a diaphragm using resistive, capacitive or inductive methods. Moreover, the blood pressure sensor can be integrated in an RFID tag and can be mounted or formed on a component of the perfusion device 10, for example, on the balloon 18. The sensor can comprise a radiofrequency LC circuit comprising a capacitive pressure sensor that serves as a variable capacitor. In use, a change in pressure mediates a change in the resonant frequency of the sensor and is transmitted by RF signals to a detector 34 held near the body.

Figure 6A:
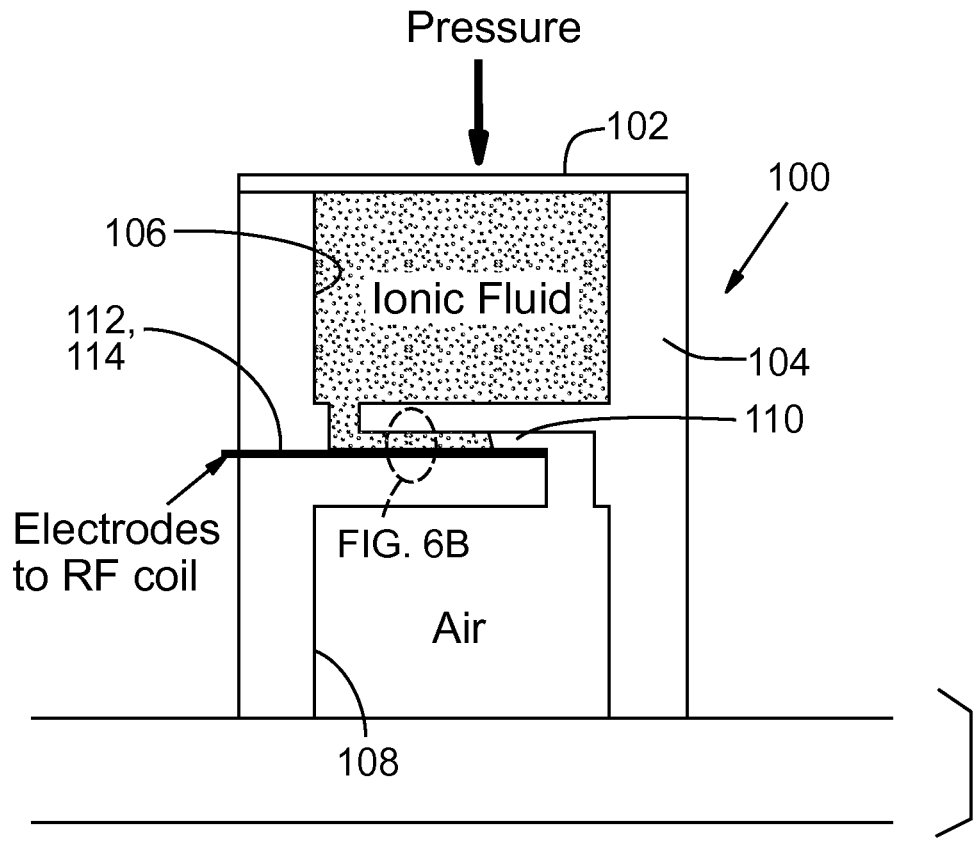
FIG. 6A is a cross-sectional view of a blood pressure sensor, according to one embodiment.
Figure 6B:
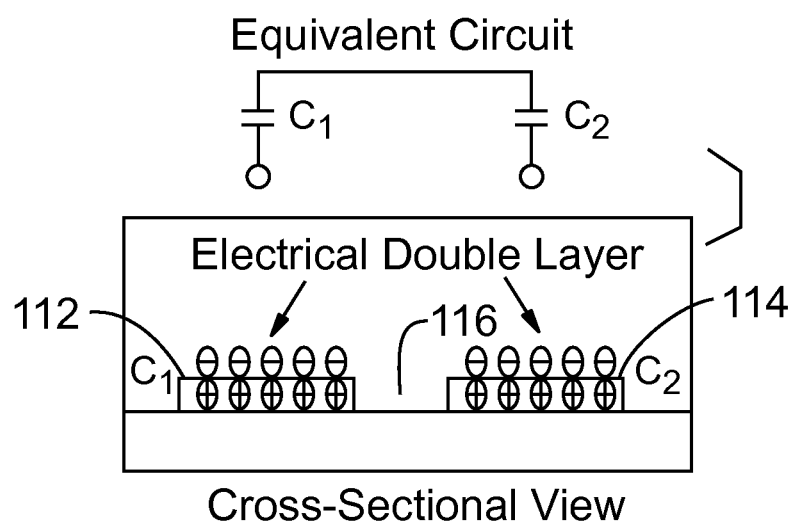
FIG. 6B is an enlarged cross-sectional view of a micro-channel of the blood pressure sensor.

FIGS. 6A and 6B schematically illustrate the configuration and operation of a blood pressure sensor 100, according to one specific implementation. The sensor 100 comprises a flexible diaphragm 102 mounted to a sensor body 104, which defines a first fluid chamber 106, a second fluid chamber 108, and a microchannel 110 extending between and being in fluid communication with the chambers 106, 108. The first fluid chamber 106 can be filled with a conductive (ionic) liquid and has an upper opening sealed by the diaphragm 102. The second fluid chamber 108 can be filled with a suitable pressurized gas, such as air. An inlet of the microchannel 110 is open to the first chamber 106 and an outlet of the microchannel 110 is open to the second chamber 108 so as to allow the conductive fluid to flow into the microchannel upon application of pressure on the diaphragm 102. A surface of the microchannel 110 is formed with two spaced apart electrodes 112, 114 (e.g., indium tin oxide electrodes) defining a gap 116 therebetween extending lengthwise of the microchannel from the inlet to the outlet. The electrodes 112, 114 can be electrically connected to a radiofrequency (RF) coil of the sensor.

When the blood pressure sensor 100 is implanted in the body, the diaphragm 102 is exposed to and arranged in parallel to the blood flow so that it deflects under the static pressure of the blood flow and forces the conductive fluid in the first chamber 106 to flow into the microchannel 110. As the conductive fluid flows into the microchannel, the interfacial areas between the electrodes 112, 114 and fluid increase and so do the capacitances between the two electrodes. The equivalent circuit between the electrodes is shown in FIG. 6B. Here, electrical double layers, which spontaneously form on the electrode surfaces as the conductive fluid flows along the length of the microchannel, serve as capacitors. The conductive liquid electrically connects the two double layers serving as an electrode for each double layer capacitor. In general, the thickness of the electrical double layers is in the nanometer range, which means that the capacitances are much higher than those found in other conventional or microscale capacitors since the capacitance is inversely proportional to the separation between conductors. This results in extremely high sensitivity in the present pressure sensing. The span of the capacitance can be controlled by adjusting the microchannel dimensions. Since the capacitance is proportional to how far the fluid flows into the microchannel, decreasing the height of the microchannel will provide a larger change in the interfacial area and thus capacitance for a given displaced fluid volume. At the same time, the height of the microchannel should be sufficient to minimize pressure drop, so as not to compromise the response time of the sensor. The compressed gas in the second chamber 106 acts as a buffer, allowing the conductive fluid to easily move back and forth in the microchannel as the external pressure on the diaphragm changes. The electrodes 112, 114 serve as the terminals to a wireless LC circuit, which can include an inductive coil printed on a surface of the sensor.

Figure 7A:
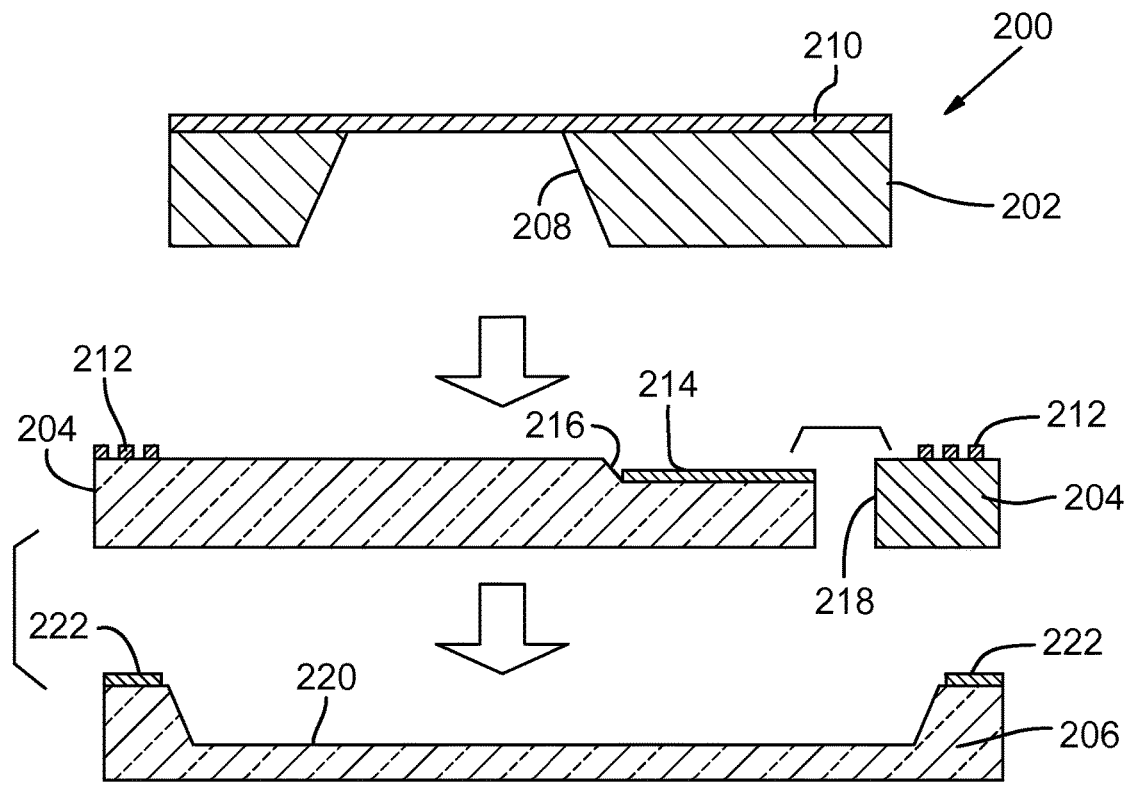
FIGS. 7A and 7B are cross-sectional views illustrating the formation and assembly of multiple layers forming a blood pressure sensor.
Figure 7B:
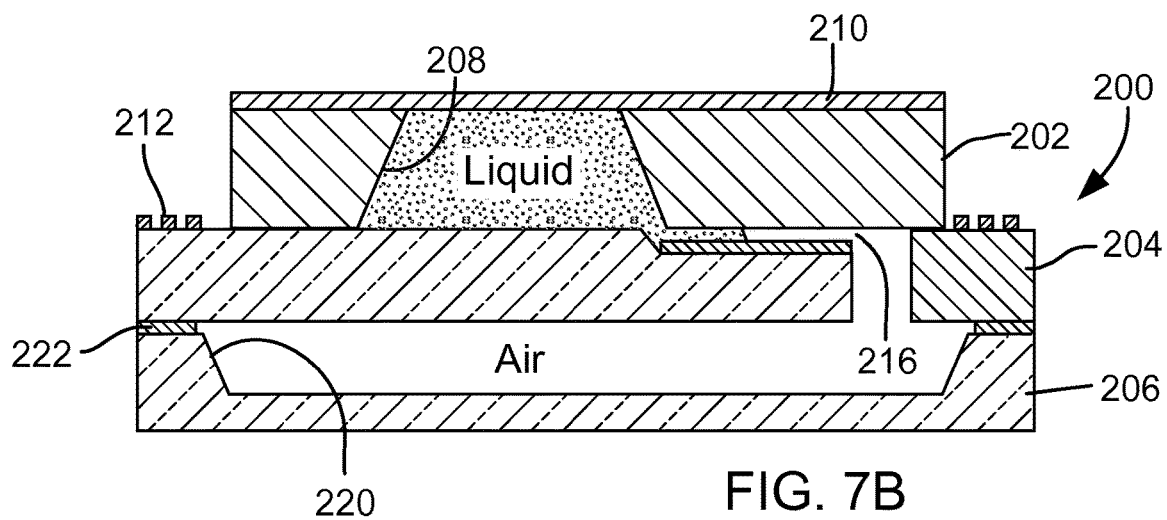

The blood pressure sensor can be made using microelectromechanical (MEMS) fabrication techniques. For example, referring to FIGS. 7A and 7B, a blood pressure sensor 200 comprises an upper, first layer 202, an intermediate, second layer 204, and a lower, third layer 206. The layers 202, 204, 206 can be fabricated separately and subsequently assembled and secured to each other as shown in FIG. 7B. The first layer 202 can be formed from a silicon substrate having a silicon nitride membrane 210 (a $Si_3N_4$ membrane) on an upper surface thereof. Backside KOH etching can be used to form a chamber 208 that is open to the lower surface of the first layer 202. The membrane 210 serves as the diaphragm of the sensor.

The intermediate layer 204 can be formed from a glass substrate and can serve as a support for an antenna 212 and electrodes 214. Using a wet etching method, a recessed surface for a microchannel 216 can be formed in the glass substrate, followed by depositing and patterning of the electrodes 214 on the recessed surface. An aperture or hole 218 in the intermediate layer 204 can be made by drilling. A suitable metal can be deposited in a spiral pattern along the outer edge of the upper surface of the intermediate layer 204 to form the coils of the antenna. Both terminals of the antenna coils can be electrically connected to the electrodes in the microchannel, such as by respective traces on the intermediate layer 204. In order to minimize the ohmic resistance of the antenna, electroplating can be used for depositing the antenna.

Another glass plate can be used to form the third layer 206, which can be wet-etched to form a lower chamber 220. The three layers 202, 204, 206 can be assembled by bonding the first layer 202 to the intermediate layer 204 using, for example, anodic bonding, after which the chamber 208 can be filled with an ionic liquid. The third layer 206 can then be joined to the lower surface of the intermediate layer 204 using, for example, a suitable adhesive 222.

Figure 8:
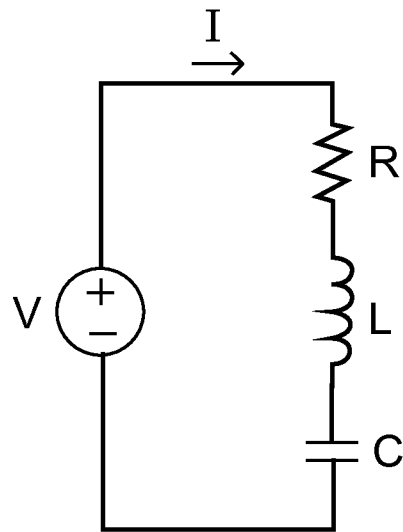
FIG. 8 is a schematic of an RLC circuit.

The sensor can be treated as the capacitive element of an L-C oscillator circuit, which enables its use as a passive device. A simple RLC circuit is depicted in FIG. 8. The voltage source is coupled with the inductor as the circuit receives energy from the external transmitter (e.g., detector 34), the capacitor is related to the transducer, and the resistance (usually low) is inherent in the device. The governing equation for this circuit is $$\frac{d^2 i(t)}{dt^2} + \frac{R}{L}\frac{di(t)}{dt} + \frac{1}{LC}i(t) = 0$$

Figure 9:
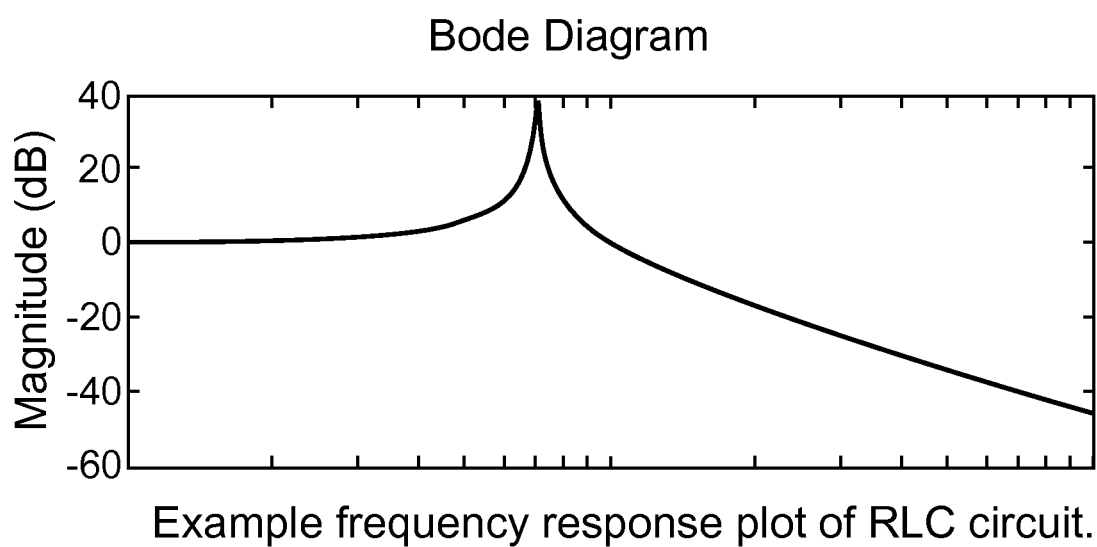
FIG. 9 is an exemplary frequency response plot of an RLC circuit.

As the system is excited from an external source, the current oscillates at the natural frequency of the system, $\sqrt{1/LC}$. Changing the capacitance or inductance changes the frequency, which can be detected when an inductively-coupled signal is received from the device. An example of the frequency response plot for an RLC circuit is shown in FIG. 9. For a high frequency system, this can be done repeatedly and continuously to monitor the changes in the sensor as pressure changes, or alternatively, transient behavior of the sensor can be monitored as opposed to the steady state behavior shown in FIG. 9. Given the short duration of use in certain applications, an active sensor and circuit design can be employed, which can improve time response (to capture continuous pressure measurements) and signal strength. For example, a capacitive bridge measurement technique can be employed or the change in capacitance can be directly transmitted rather than relying on the incoming energy from the monitor.

Thus, the blood pressure sensor can translate changes in pressure into resonant radiofrequency signals that can be detected by the external monitor 34. The monitor 34 can be programmed with software that processes the received signals and generates dynamic and physiologic blood pressure and heart rate readings. As shown in FIG. 5, the monitor 34 can have a visual display that displays the patient's physiological characteristics being monitored, as well the position of one of the position markers. The monitor can include a suitable microprocessor that can be programmed with software. In some embodiments, the monitor 34 can be a portable computer, such as a tablet computer, a smart phone, or a laptop computer.

In particular embodiments, a sensor assembly can comprise a position sensor (e.g., an RFID tag) and a blood pressure sensor that are electrically connected to a common antenna (e.g., antenna 212). Where a common antenna is used, the blood pressure signal can be used as the locating signal for position sensor; in other words, the position of the monitor 34 where the strongest blood pressure signal is detected is related to the position of the sensor in the body. If the device is active, the blood pressure sensor can be switched in and out of the antenna circuit, allowing the one antenna to function with both the position sensor and the blood pressure sensor. In an alternative embodiment, a sensor assembly can comprise a position sensor (e.g., an RFID tag) having a first antenna and a blood pressure sensor having a second antenna, wherein the first and second antennas are physically and electrically separated, such as by forming the antennas on separate layers of the device or by forming one antenna coil concentrically within another antenna coil.

FIGS. 10 and 11 are perspective and cross-sectional views of a perfusion device 300, according to another embodiment. The perfusion device 300 comprises a an expandable sealing member main body 302 comprising a self-expanding stent, or frame, 304 and a blood-impermeable tubular cover, liner or sleeve 306 supported on and covering the stent 304. The cover 306 can comprise any of various biocompatible fabrics, such as fabrics formed from polyethylene terephthalate (PET), polytetrafluoroethylene (PTFE), polyester urethane urea (PEUU), poly(carbonate urethane) urea (PCUU) or polyurethane fibers, or other types of synthetic fibers. The cover 306 alternatively can be a non-woven sheet of material made of any of these synthetic materials. Still alternatively, the cover 306 can be made of a blood-impermeable natural tissue, such as pericardium, or a thin metal film (e.g., Nitinol). The cover 306 can be secured to the stent 304 using suitable techniques, such as sutures, welding, or an adhesive.

The cover 306 is shown as being mounted on the outside of the stent 304, but can be mounted on the inside of the stent in alternative embodiments.

The stent 304 can be a spiral wire as shown but can have configurations as well, such as a lattice or mesh type configuration similar to a coronary stent. The stent 304 can be made of Nitinol, stainless steel, cobalt chromium alloy or various other suitable materials. The perfusion device 300 can further include a plurality of rods or wires 308, the distal ends of which are connected to the main body 302. The wires 308 are long enough to extend out of the patient's body such that the proximal end portions of the wires can be manipulated by the user by application of pushing or pulling forces on the wires. In this regard, the proximal end portions of the wires 308 can be connected to a handle to facilitate insertion and withdrawal of the perfusion device from the patient's body. The perfusion device 300 can be used with an introducer sheath 310 which facilitates insertion of the perfusion device into the patient's vasculature and subsequent withdrawal of the device.

FIGS. 12A-12C illustrate use of the perfusion device 300 to treat a rupture of the descending aorta A. As shown in FIG. 12B, the introducer sheath 310 is first inserted into the patient's vasculature, such as via a femoral artery of the patient. The introducer sheath 310 can have a length sufficient to extend to a location in the descending aorta while a proximal end portion (not shown) remains outside the body. The perfusion device 300 can then be inserted through the introducer sheath 310 and into the descending aorta until the main body 302 extends over and seals the ruptured portion of the aorta. As the main body 302 merges from the distal opening of the sheath 310, it expands to its functional size contacting the inner wall of the aorta. The main body 302 can include one or more position markers 32 (e.g., RFID tags) as described above to help position the main body within the aorta. Once implanted, blood is caused to flow into the distal end of the main body, through the lumen of the main body, and outwardly through the proximal opening of the main body (in the direction of arrows 312 in FIG. 10), thereby bypassing the ruptured portion of the vessel. The patient can then be transported to a medical facility for surgery to repair the ruptured vessel.

Referring to FIG. 12C, the perfusion device 300 can be removed from the patient by retracting the wires 308 proximally and/or pushing the introducer sheath 310 distally to pull the main body 302 back into the sheath. Relative movement between the wires and the sheath causes the sheath to apply a radial force against the wires, forcing the wires to collapse radially, which in turn collapses the proximal end of the main body 302 enough to be pulled through the distal opening of the sheath. Further retraction of the wires pulls the main body back through the sheath and out of the patient's body.

Figure 13:
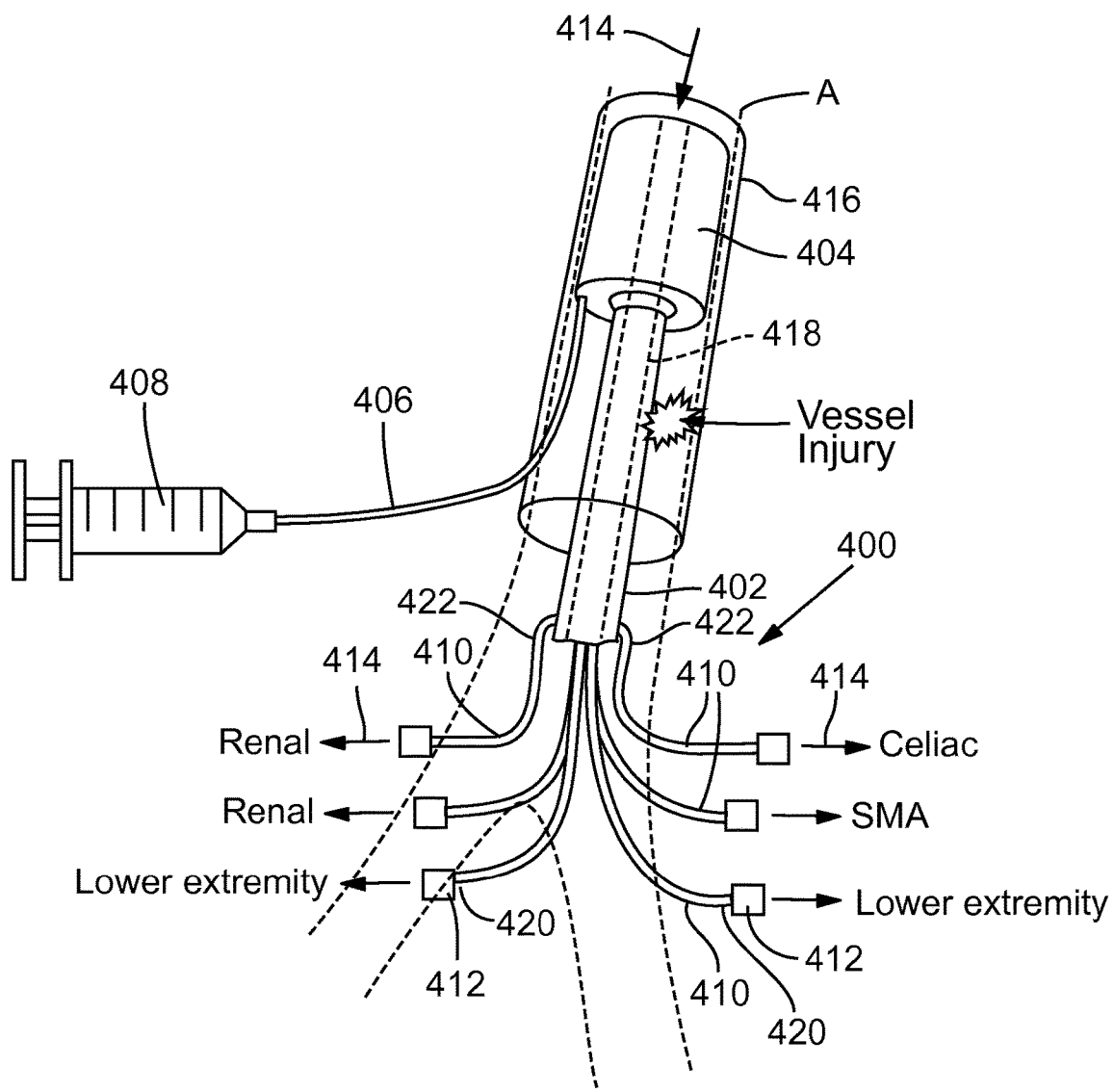
FIG. 13 is a perfusion device, according to another embodiment, that can be used to perfuse blood from the descending aorta to downstream branch arteries during complex open aortic repair.

FIG. 13 shows a perfusion device 400, according to another embodiment. The perfusion device 400 is configured to be implanted in the aorta and allow for the perfusion of blood from the descending aorta to downstream branch arteries during complex open aortic repair, in lieu of an aortic clamp or a left heart bypass. The perfusion device 400 can be used for open aortic repair in both military (for repairing trauma to the aorta) and civilian (for treating aneurysms) settings.

The perfusion device 400 in the illustrated embodiment comprises an elongated shaft 402 and an inflatable balloon 404 mounted on the distal end portion of the shaft 402. The shaft 402 can extend from a distal end to a proximal end (not shown) outside the body. The perfusion device 400 can also include an inflation conduit 406 having a distal end fluidly connected to the balloon 404 and a proximal end fluidly connected to a syringe 408 or another source of an inflation fluid that is configured to pump the inflation fluid through the conduit and into the balloon.

The perfusion device 400 also comprises one or more secondary perfusion conduits, or cannulas, 410, which are in fluid communication with a lumen 418 of the shaft 402. The secondary fluid conduits 410 can comprise flexible tubular members, and can be made from any of various polymeric materials, such as polyurethane. The proximal end 420 of each secondary conduit 410 is configured to be positioned within a respective branch artery (e.g., a renal artery, the celiac artery, an artery feeding a lower extremity, or the superior mesenteric artery), as depicted in FIG. 13. In the illustrated embodiment, the perfusion device includes six secondary conduits 410: two for renal artery perfusion, two for visceral branches (superior mesenteric and celiac arteries) and two for distal aortic (lower extremity and spinal cord) perfusion. In alternative embodiments, the perfusion device can include a greater or fewer number of secondary conduits, which can be positioned in other branch arteries.

To assist in retaining the proximal end portion of each secondary conduit within a branch artery, an inflatable balloon 412 can be mounted on the proximal end portion 420 of each conduit. Each balloon 412 can be fluidly connected to separate source of an inflation fluid or to a common source (e.g., the syringe 408) by respective inflation-fluid conduits or a common inflation-fluid conduit.

The shaft 402 has a perfusion lumen 418 for the flow of blood that extends from a distal opening of the shaft (which is proximate the distal end of the balloon 404) to a location downstream of the balloon 404 where the lumen is in fluid communication with the secondary fluid conduits 410. For example, the distal ends 422 of the conduits 410 can extend through side ports in the shaft into the perfusion lumen. Thus, a pathway for blood extends from the distal end of the shaft, through the shaft lumen 418, and into and through each of the conduits 410. In alternative embodiments, the shaft 402 can be formed with multiple lumens extending from the distal end of the shaft to each of the secondary conduits 410. In other embodiments, one or more of the conduits 410 can extend from another conduit 410 to divert a portion of blood flow from one conduit to another. For example, the distal end 422 of a first conduit 410 can be fluidly connected to a second conduit 410 at a location proximal to the distal end 422 of the second conduit, such that a portion of blood flowing into the second conduit is diverted into the first conduit.

Each balloon 404, 412 can include one or more anchors (e.g., anchors 30 shown in FIG. 4) to engage the inner walls of the vessels and/or can be formed with a relatively rough outer surface to increase the coefficient of friction of the balloon material against the vessel wall to increase resistance against balloon migration.

Also, instead of providing a separate inflation conduit 406, the shaft 402 can be formed with a separate inflation lumen that extends from the balloon 404 to a proximal end of the shaft outside the body. The proximal end of the inflation lumen can be fluidly connected to a source of an inflation fluid (e.g., a syringe) to pump the inflation fluid through the inflation lumen and into the balloon 404. In addition, the inflation lumen in the shaft 402 can be in fluid communication with respective inflation lumens that are formed in and extend through each of the secondary conduits 410 to a respective balloon 412.

In use, such as during complex open aortic repair, the perfusion device 400 is placed in the aorta A such that the balloon 404 is upstream of a vessel injury or aneurysm to be repaired and the junction of the distal ends 422 of the secondary conduits 410 with the shaft 402 is downstream of the vessel injury or aneurysm. The proximal ends 420 of the secondary conduits 410 can be positioned in respective branch arteries and the balloons 412 can be inflated to help retain the proximal ends of the secondary conduits 410 in the branch arteries. The balloons 412 can be sized such that in their inflated state, the outer diameter of the balloons can contact and frictionally engage the inner walls of the branch arteries. Once the balloons 404, 412 are inflated, blood is caused to flow into the open distal end of the shaft 402, through the shaft lumen 418, through the secondary conduits 410 and into the branch arteries containing the secondary conduits, thereby bypassing the vessel injury or aneurysm. In certain embodiments, the shaft 402 can have side ports positioned proximally of the balloon (e.g., side ports 26 in FIG. 1) in communication with the lumen 418 to allow antegrade blood to flow outwardly through the side ports into aorta downstream of the vessel injury. The vessel injury or aneurysm can then be repaired using known surgical techniques, such as by suturing a prosthetic graft 416 over the injured/diseased portion of the aorta.

As noted above, the conventional clamp and sew approach used during open aortic repair increases the risk for organ failure, lower extremity ischemia and paraplegia. Conventional distal aortic perfusion by means of a left heart bypass entails increased complexity including additional perfusion equipment, expertise on the part of the surgeon and additional operative exposure. Further, the necessary equipment may not be available at many facilities. Advantageously, deployment of the perfusion device 400 is less complicated than performing a left heart bypass while allowing perfusion of the distal aorta and individual visceral vessels, thereby minimizing risk of organ failure, ischemia and paraplegia.

Figure 14A:
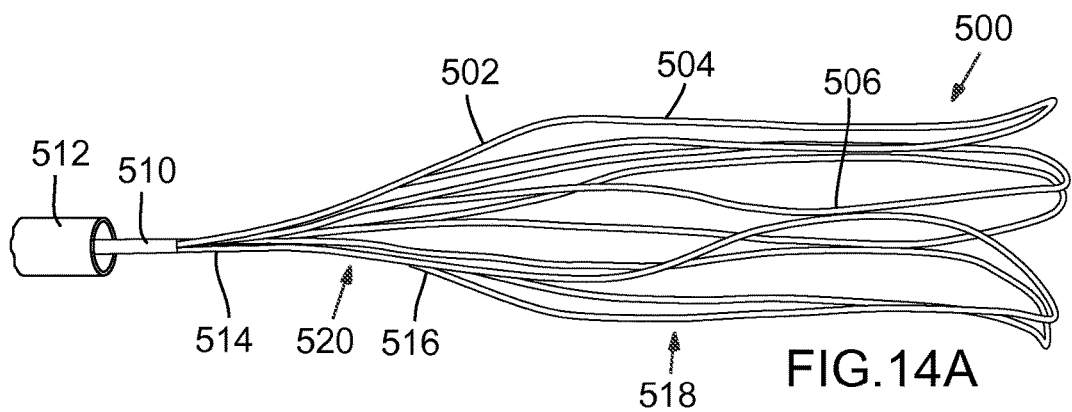
FIGS. 14A-14D are various views of a perfusion device, according to another embodiment.
Figure 14B:
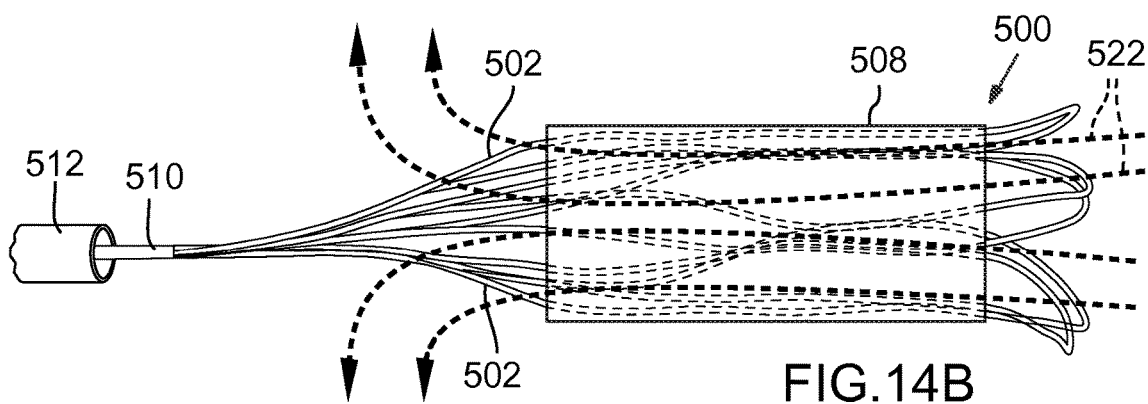
Figure 14C:
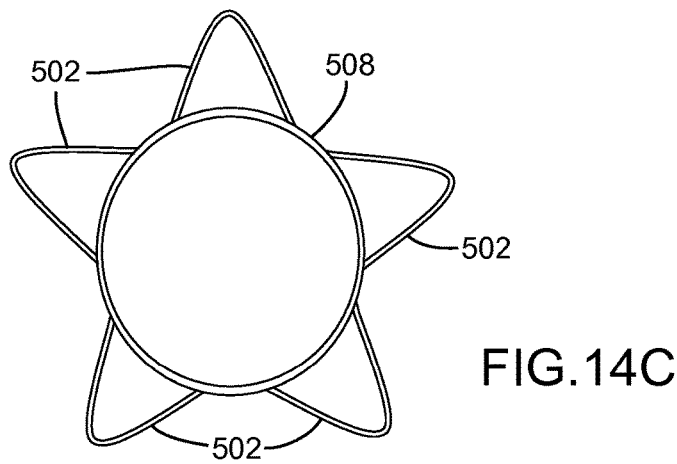
Figure 14D:
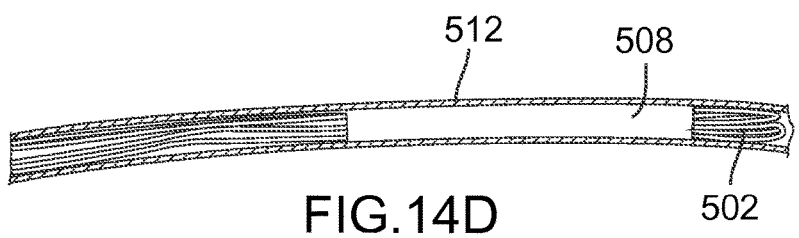

FIGS. 14A-14D show the distal end portion of a perfusion device 500, according to another embodiment. The perfusion device 500 comprises a sealing member in the form of a self-expandable wire stent or frame 502 and a blood-impermeable cover or sleeve 508 mounted on the outside of the frame 502 (as shown in FIG. 14B). FIG. 14A shows the frame 502 without the cover 508 for purposes of illustration. The frame 502 in the illustrated embodiment is formed from a plurality of petal-shaped wires 504. Each wire 504 in the illustrated embodiment forms a longitudinally extending loop have a first end portion 514 and a second end portion 516 secured to the first end portion 514. The longitudinally extending loops can be circumferentially arranged and secured to each other along their adjacent edges at junctions 506. The stent 502 can have a generally cylindrical distal end portion 518 and a tapered proximal end portion 520 to facilitate recapture of the stent into a sheath 512. The cover 508 can extend over and cover at least the majority of the length of the cylindrical portion 518 as shown in FIG. 14B, but also can extend over and cover a portion or the entire length of the tapered portion 520.

The device 500 can further include a shaft 510, the distal end of which is fixedly secured to the proximal end portions 514 of the wires 504 of the frame. The shaft 510 has a length sufficient to extend through a patient's vasculature to position the sealing member at the location of an injury to a blood vessel. The proximal end of the shaft 510 can be coupled to a handle to facilitate advancement and retraction of the device within the patient's vasculature. Alternatively, the wires 504 can extend all the way to the handle outside the body without a separate shaft coupling the wires to the handle. The device can include one or more position markers (e.g., RFID tags) mounted at a convenient location, such as on the distal and proximal end portions of the cover 508.

In one specific implementation, the wires 504 of the frame can be made of a shape-memory material, such as Nitinol, but can be formed from other suitable materials, such as stainless steel, or a cobalt chromium alloy. In one specific implementation, the cover 508 can be a thin metal film (e.g., Nitinol) affixed to the wires of the frame, such as by welding. In other embodiments, the cover 508 can comprise any of various biocompatible fabrics, such as fabrics formed from polyethylene terephthalate (PET), polytetrafluoroethylene (PTFE), polyester urethane urea (PEUU), poly(carbonate urethane) urea (PCUU) or polyurethane fibers, or other types of synthetic fibers. The cover 506 alternatively can be a non-woven sheet of material made of any of these synthetic materials, or a blood-impermeable natural tissue, such as pericardium. In the illustrated embodiment, the cover 508 is shown mounted to the outside of the frame, however, in alternative embodiments, the cover 508 can be mounted to the inside of the frame.

The frame 502 is configured to be self-expandable from a radially compressed or collapsed state (FIG. 14D) to a radially expanded, deployed state (FIG. 14B). The device 500 can further include a delivery sheath 512 that extends over the frame 502 and retains it in the radially collapsed state for delivery through the patient's vasculature.

The device 500 can be used to treat a ruptured blood vessel in the manner described above with reference to FIGS. 12A-12C. With the frame retained in a collapsed state within the sheath 512, the perfusion device 500 can be inserted into a patient's vasculature (e.g., into a femoral artery) via an introducer sheath 310. The shaft 510 (or handle attached to the proximal end of the shaft) can be used to push the perfusion device 500 through the introducer sheath 310 and the patient's vasculature until the distal end portion of the perfusion device is in the vicinity of the ruptured portion of the blood vessel. To deploy the frame at the site of a vessel injury, the user can push the shaft 510 distally and/or retract the sheath 512 proximally to advance the frame from the distal opening of the sheath, allowing the frame to self-expand such that the cover 508 forms a seal against the inner wall of the vessel. Once deployed, blood can flow through the lumen defined by the cover 508 in the direction indicated by arrows 522. After treatment of the blood vessel, the frame can be retracted back into the sheath 512 and the perfusion device 500 can be removed from the patient's body.

EXAMPLE

Figure 15:
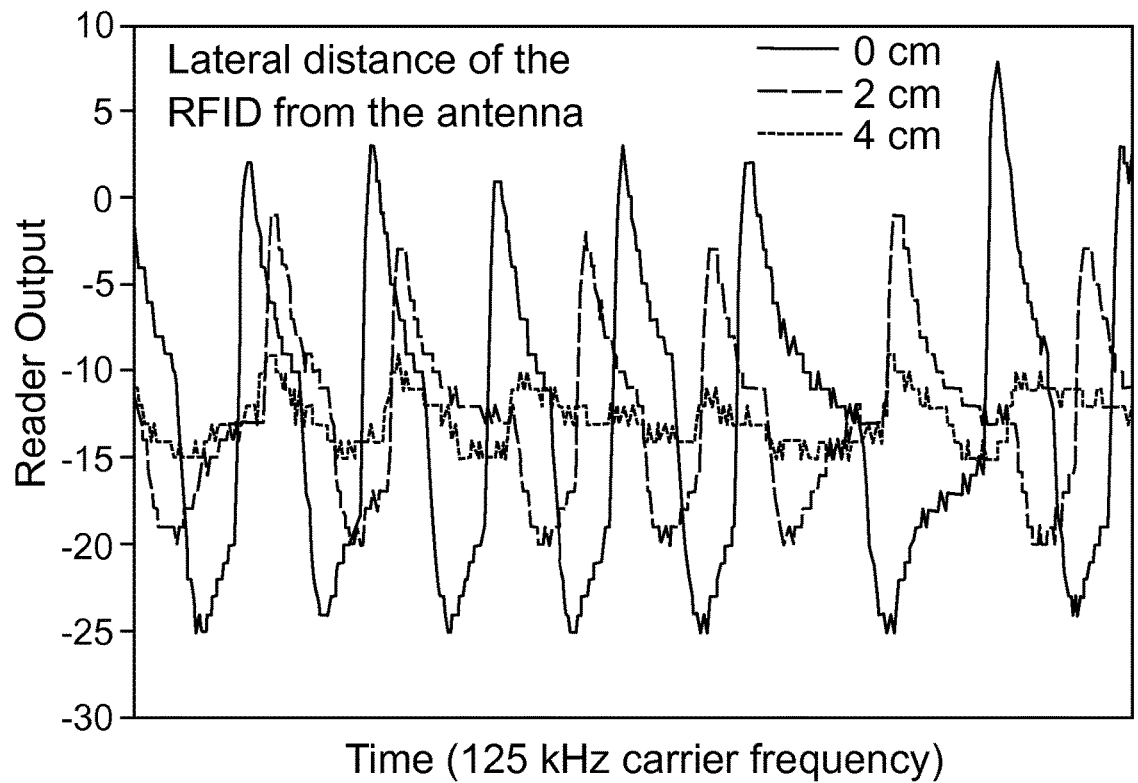
FIG. 15 is a graph showing signal outputs of an RFID reader being used to detect an RFID tag at different lateral distances from the tag.

In one example, a commercially-available RFID, low frequency tag (2-mm diameter and 1-cm long, frequency 125 kHz) and monitor were used to simulate positioning of a perfusion device within the body. To simulate localization, a stack of paper and a plexiglass sheet (total 3 cm thick) were placed between the monitor antenna and RFID tag. The tag was placed at different distances from the center of the monitor antenna, which was measured by the ruler on the plexiglass. The signal output at the monitor vs. the lateral distance from the antenna center is shown in FIG. 15. All of the wave profiles were modulated according to the data stored in the tag. In particular, the amplitude of signal output was found to monotonically decrease as the distance increased. When the tag was placed right above the center of the antenna, the amplitude was maximized. In other words, the point of maximal signal indicates to the user the location of the radiofrequency tag in the body. From the data shown, the change in signal magnitude allows localization (positioning) of a perfusion device well within a +/−2 cm range.

The optimal detection distance in this example was 3 cm. The detection distance is closely related to the induced voltage in the tag antenna ($V_{tag}$) that has to be high enough to activate and energize the tag circuit. In inductive coupling in LF and HF tag communication, the tag voltage is calculated as follows:

$$V_{tag} = 2\pi f N Q B S \cos \alpha,$$

where f is the frequency of carrier signal, S the area of the tag coil, Q the quality factor of the resonant circuit, B the strength of the magnetic field at the tag, and $\alpha$ the angle of the magnetic field normal to the tag. Due to the size restriction in the tag, there is not much room in changing S and N for the fixed frequency. However, B can be relatively easily increased by changing the current and area of the monitor antenna. The increased voltage in the tag can allow an increase in the detection distance for improved clinical performance. The angle of the magnetic field normal to the tag area ($\alpha$) effects the detection distance, as the tag voltage is a cosine function of $\alpha$. In this example, $\alpha$ was set to 90 degrees so that the tag could be activated over a distance of at least 3 cm. However, the detection distance would be decreased if the angle $\alpha$ is not maintained during use.

Thus, in particular embodiments, the perfusion device can include multiple RFID tags with different IDs spaced circumferentially around the balloon. The tags can be scanned one at a time. Among the multiple tags, the best-aligned tag provides a maximum output and thus maximum detection distance, which then can be used for subsequent positioning of the balloon.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically coupled or linked and does not exclude the presence of intermediate elements between the coupled items absent specific contrary language.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A perfusion device for treating a ruptured blood vessel of a patient, comprising:
   at least one elongated member extending from a proximal end portion to a distal end portion;
   a handle coupled to the proximal end portion of the at least one elongated member; and
   an expandable sealing member affixed to the distal end portion of the elongated member, the sealing member having a blood-impermeable surface configured to form a seal along an inner surface of the blood vessel adjacent a ruptured portion of the blood vessel when the sealing member is deployed from a radially collapsed state to a radially expanded, deployed state inside the vessel to control bleeding through the ruptured portion of the vessel;
   wherein the sealing member permits the antegrade flow of blood through the sealing member from a location upstream of the ruptured portion of the vessel to a location downstream of the ruptured portion of the vessel;
   wherein the sealing member is configured to be radially collapsible from the deployed state to the radially collapsed state for removal of the sealing member from the patient's body; and
   wherein the handle is spaced from the expandable sealing member by the at least one elongated member and is a non-expandable portion of the perfusion device, and wherein the at least one elongated member is sized such that the handle remains outside of the patient's body and remains coupled to the at least one elongated member when the sealing member is deployed inside the blood vessel and when the sealing member is radially collapsed for removal from the patient's body.

2. The perfusion device of claim 1, wherein the sealing member comprises a self-expandable stent and a blood-impermeable sleeve supported by the stent.

3. The perfusion device of claim 2, wherein the at least one elongated member comprises a plurality of wires coupled at their distal end portions to the stent and coupled at their proximal end portions to the handle.

4. The perfusion device of claim 2, wherein the stent comprises a plurality of wires, each wire has a first end portion and a second end portion secured to the first end portion so as to form a longitudinally extending loop, the loops being circumferentially arranged and secured to each other.

5. The perfusion device of claim 1, wherein the at least one elongated member comprises an elongated shaft and the sealing member comprises an inflatable balloon mounted on the shaft, the shaft having a distal opening, one or more side ports located along the shaft between a proximal end of the balloon and the proximal end portion of the shaft, and a lumen in fluid communication with the distal opening and the one or more side ports such that a perfusion pathway for the flow of blood extends from the distal opening, through the lumen and outwardly through the side ports.

6. The perfusion device of claim 1, further comprising one or more RFID tags configured to emit radiofrequency waves through the patient's body to assist in positioning the sealing member at a desired location within the patient's vasculature.

7. The perfusion device of claim 6, wherein the one or more RFID tags comprises a first RFID tag mounted adjacent a distal end of the sealing member and a second RFID tag mounted adjacent a proximal end of the sealing member.

8. The perfusion device of claim 6, further comprising a blood pressure sensor configured to measure the pressure of blood in the vessel.

9. The perfusion device of claim 8, wherein at least one of the one or more RFID tags and the blood pressure sensor are electrically connected to a common antenna.

10. The perfusion device of claim 6, further comprising a detector configured to receive radiofrequency waves emitted from the one or more RFID tags.

11. The perfusion device of claim 10, further comprising a sensor configured to emit a signal corresponding to a physiological parameter of the patient, and wherein the detector is configured to detect the signal and provide visual indicia representative of the physiological parameter.

12. The perfusion device of claim 10, wherein the detector is a portable, hand held unit.

13. The perfusion device of claim 1, wherein the sealing device has a length of at least 10 cm.

14. The perfusion device of claim 1, wherein the blood-impermeable surface comprises a generally cylindrically shaped outer surface of the sealing member configured to form a seal along the entire inner surface of the blood vessel from a distal end of the outer surface to a proximal end of the outer surface.

15. The perfusion device of claim 1, further comprising one or more position sensors configured to permit a user to detect the position of the sealing member within the patient's vasculature.

16. A method of treating a ruptured blood vessel of a patient, comprising:
inserting a perfusion device into the vasculature of the patient, the perfusion device comprising at least one elongated member having a distal end portion and a proximal end portion, a radially expandable sealing member coupled to the distal end portion of the elongated member, and a handle coupled to the proximal end portion of the elongated member;
advancing the perfusion device through the patient's vasculature until the sealing member is adjacent the ruptured portion of the blood vessel; and
radially expanding the sealing member such that a blood-impermeable outer surface of the sealing member forms a seal along an inner wall of the blood vessel and covers the ruptured portion of the vessel, the perfusion device providing a perfusion pathway extending from an inlet at a location upstream of the ruptured portion of the vessel through the sealing member to an outlet at a second location downstream of the ruptured portion of the vessel causing antegrade blood to flow into the inlet, through the sealing member, and outwardly through the outlet within the confines of the vessel downstream of the ruptured portion of the vessel;
wherein the handle remains outside the patient's body and coupled to the elongated member during the acts of inserting, advancing and radially expanding the sealing member.

17. The method of claim 16, wherein the sealing member comprises a self-expandable stent and a blood-impermeable sleeve supported by the stent, and the act of radially expanding the sealing member comprises deploying the stent from a radially collapsed state to a radially expandable state such that the sleeve forms a seal along an inner wall of the blood vessel and covers the ruptured portion of the vessel, the stent having an inlet opening and outlet opening, the inlet opening defining the inlet of the perfusion pathway and the outlet opening defining the outlet of the perfusion pathway.

18. The method of claim 17, wherein the stent comprises a plurality of wires, each wire forming a longitudinally extending loop, the loops being circumferentially arranged and secured to each other.

19. The method of claim 16, wherein:
the at least one elongated member comprises an elongated shaft and the sealing member comprises an inflatable balloon mounted on the shaft, the shaft having a distal opening defining the inlet of the perfusion pathway, one or more side ports located along the shaft between a proximal end of the balloon and a proximal end portion of the shaft defining the outlet of the perfusion pathway, and a lumen in fluid communication with the distal opening and the one or more side ports such that the perfusion pathway for the flow of blood extends from the distal opening, through the lumen and outwardly through the side ports.

20. The method of claim 16, wherein the ruptured blood vessel is the descending aorta and the perfusion device is inserted into the patient's vasculature via a femoral artery and advanced through the patient's vasculature until the sealing member is positioned within the descending aorta.

21. The method of claim 20, wherein the sealing member has a length of at least 10 cm.

22. The method of claim 16, wherein the act of advancing the perfusion device comprises detecting the position of one or more position sensors on the perfusion device with a detection device located outside of the body and positioning the sealing member within the vessel based on the position of the one or more position sensors.

23. The method of claim 22, further comprising detecting the position of the one or more position sensors relative to one or more external landmarks on the patient's body and positioning the sealing member within the vessel based on position of the one or more position sensors relative to the one or more external landmarks on the patient's body.

24. The method of claim 22, wherein the one or more position sensors comprise RFID tags.

25. The method of claim 22, wherein the one or more position sensors comprises a first position sensor mounted on a distal end portion of the sealing member and a second position sensor mounted on a proximal end portion of the sealing member.

26. The method of claim 22, wherein at least one of the one or more position sensors comprises an integrated position sensor and blood pressure sensor.

27. The method of claim 16, wherein the perfusion device comprises a blood pressure sensor configured to measure the pressure of blood in the vessel.

28. The method of claim 16, further comprising radially collapsing the sealing member and removing the sealing member from the patient's body, wherein the handle remains outside the patient's body and coupled to the elongated member during the acts of inserting, advancing, radially expanding, radially collapsing and removing the sealing member from the patient's body.

\* \* \* \* \*